United States Patent [19]

Partain, III. et al.

[11] Patent Number: 4,946,870
[45] Date of Patent: Aug. 7, 1990

[54] DELIVERY SYSTEMS FOR PHARMACEUTICAL OR THERAPEUTIC ACTIVES

[75] Inventors: Emmett M. Partain, III., Bound Brook; George L. Brode, II., Bridgewater, both of N.J.

[73] Assignee: Union Carbide Chemicals and Plastics Company Inc., Danbury, Conn.

[21] Appl. No.: 268,871

[22] Filed: Nov. 8, 1988

Related U.S. Application Data

[63] Continuation-in-part of Ser. No. 189,312, Feb. 3, 1988, which is a continuation of PCT US87/001,246, which is a continuation-in-part of Ser. No. 871,381, Jun. 6, 1986, abandoned.

[51] Int. Cl.$^5$ .................. A61K 9/02; A61K 9/06; A61K 9/12; A61K 31/715
[52] U.S. Cl. ................. 514/777; 514/55; 514/947; 514/953; 514/969; 514/945; 514/944; 424/DIG. 15; 424/443; 424/444; 424/449
[58] Field of Search ............... 514/55, 947, 953, 777, 514/944, 945, 969, 953; 536/20; 527/300, 313, 314; 424/443, 444, 449, DIG. 15

[56] References Cited

U.S. PATENT DOCUMENTS

| | | |
|---|---|---|
| 2,795,579 | 6/1957 | Docri ............................ 536/20 |
| 3,953,608 | 4/1976 | Vanlerberghe et al. ............... 536/20 |
| 4,336,070 | 6/1982 | Koshugi .............................. 536/20 |
| 4,365,050 | 12/1982 | Ivani ................................. 527/314 |
| 4,424,346 | 1/1984 | Hall et al. ........................ 536/20 |
| 4,532,267 | 7/1985 | Allan ................................ 527/312 |
| 4,574,150 | 3/1986 | Austin .............................. 536/20 |
| 4,613,502 | 9/1986 | Turková et al. ................... 514/59 |
| 4,659,700 | 4/1987 | Jackson ............................ 536/20 |
| 4,774,091 | 9/1988 | Yamahira et al. ................ 514/953 |
| 4,780,310 | 10/1988 | Lang et al. ....................... 536/20 |

FOREIGN PATENT DOCUMENTS

| | | |
|---|---|---|
| 0115574 | of 0000 | European Pat. Off. . |
| 3501891A | 1/1985 | Fed. Rep. of Germany . |
| 3502833A | 1/1985 | Fed. Rep. of Germany . |
| 3504095A | 2/1985 | Fed. Rep. of Germany . |
| 58-755561 | 1/1985 | Japan . |

Primary Examiner—Ronald W. Griffin
Attorney, Agent, or Firm—Henry H. Gibson

[57] ABSTRACT

Delivery systems containing at least one aminopolysaccharide derivative are provided for the delivery of pharmaceutical or therapeutic actives to a desired topical or mucous membrane site in a subject, and wherein upon delivery, the systems provides a biocompatible, substantive, gas permeable, film from which actives are available at the designated site.

17 Claims, No Drawings

DELIVERY SYSTEMS FOR PHARMACEUTICAL OR THERAPEUTIC ACTIVES

CROSS REFERENCE TO RELATED APPLICATIONS

This application is a continuation-in-part of U.S. application Ser. No. 07/189,312 filed Feb. 3, 1988, which is a continuation of PCT US87/001,246, which is a continuation of PCT application Ser. No. 87/001,246, filed June 2, 1987, which is a continuation-in-part of U.S. application Ser. No. 871,381, filed June 6, 1986, now abandoned, the subject matter of both applications being hereby incorporated by reference.

FIELD OF THE INVENTION

This invention relates, in general, to novel delivery systems useful for the topical delivery of pharmaceutical or therapeutic actives. In one aspect, this invention relates to delivery systems containing certain aminopolysaccharides and derivatives thereof which are effective systems for the delivery of a variety of pharmaceutical and therapeutic actives. In a further aspect, this invention is directed to the preparation and use of such systems.

BACKGROUND OF THE INVENTION

Traditionally, pharmaceutical and therapeutic actives can be administered to the body by a number of routes including ingestion, injection, inhalation, and topical application. Absorption of an active by ingestion, injection, and inhalation generally gives systemic distribution of the active throughout the body. This systemic distribution of the active may be undesirable for three reasons. First, these modes of administration are non-specific. The active is distributed through the entire body and not localized. Secondly, there may be undesirable effects such as toxic or irritating reactions on non-target organs or regions. Finally, to achieve the desired effect at the target organ or region, a higher dosage than might otherwise be desired must be administered to compensate for systemic dilution of the active.

Because of these deficiencies, topical application of actives is a highly desirable alternative: the dosage is reduced and the active is confined to the region of the body where it is applied. Thus, systemic distribution of the active throughout the body is obviated. In contrast to systemic delivery, topical delivery refers to the application of an active in a manner so that it acts primarily at the site of application. Typical sites of topical delivery include application to the dermal, opththalmic, and mucous membranes and tissues such as the skin, eyes, ears, mouth, nose, throat, rectum, vagina and urethra.

However, despite these advantages of topical delivery, most current topical delivery formulations are not very efficient and are therefore of limited utility. There are four reasons for this inefficiency of current topical delivery technology. First, skin and mucous membranes possess good barrier properties and the permeability of most actives through these is generally poor. Second, actives applied topically are subject to migration and loss due to perspiration, natural tissue lavation and mechanical action. Third, because most pharmaceutical or therapeutic actives are relatively simple, low molecular weight compounds or mixtures, these actives are not applied alone, but in combination with a variety of additives to deliver the active to the application site and control the dosage. Fourth, the choice of a proper delivery system can minimize undesirable crystallization of the active, and hence optimize its availability in its active form. Most current topical delivery systems are petrolatum based cremes and ointments. These unctuous formulations are undesirable because they are at best uncomfortable and messy when applied, and at worst, irritating and potentially damaging to skin and mucous membranes (mucosa).

Accordingly, one or more of the following objects will be achieved by the practice of the present invention. It is an object of this invention to provide delivery systems containing pharmaceutical and therapeutic actives which can be administered to a desired topical or mucous membrane site of a subject, including human beings. Another object of this invention is to provide delivery systems comprised of certain aminopolysaccharides which may contain pharmaceutical and therapeutic actives. A further object of the invention is to provide delivery systems which avoid many of the undesirable features of ointments and salves and yet maintain and transmit the necessary amount of active ingredient to an appropriate site of the body. Another object of this invention is to provide processes for the preparation and use of the systems containing chitosan derivatives and the active component. These and other objects will readily become apparent to those skilled in the art in light of the teachings herein set forth.

SUMMARY OF THE INVENTION

As indicated above, the present invention is directed to novel delivery systems comprised of certain aminopolysaccharides including chitosan derivatives and pharmaceutical or therapeutic actives, a method for their preparation and a method for their application to a subject.

The delivery system of the present invention is a biocompatable, substantive, film-forming system for the delivery of pharmaceutical or therapeutic actives to a desired topical site of a subject or host. The system is comprised of from about 0.01 to about 99.99 weight percent of the system of at least one aminopolysaccharide selected from the group consisting of:
  (1) chitosonium polymers, and
  (2) covalent chitosan derivatives, and wherein the system after delivery to the site, provides a non-irratating, imperceptible, substantive, gas permeable, film from which the actives are available for treatment of the subject at the site. The delivery system can optionally also contain at least one pharmaceutically acceptable diluent.

DETAILED DESCRIPTION OF THE INVENTION

As indicated above, the delivery systems of the present invention encompass delivery systems based on a variety of aminopolysaccharides, particularly, chitosan derivatives, and possess a variety of useful characteristics making these materials superior for the delivery of pharmaceutical and therapeutic actives.

As used throughout the specification and appended claims a "pharmaceutical active" is considered to be a drug, i.e., a substance which when applied to, or introduced into the body alters in some way body functions. The term "therapeutic active" is broader. It is any substance which either alters body function or the cosmetic appearance but is not traditionally or technically considered a drug. For example, water may be applied to the skin as a moisturizing agent. Although not a drug in the strict sense, water in this case does alter the skin in at least a cosmetic manner or in some cases therapeutic and is considered a therapeutic active for purposes of the present invention.

As indicated there are several features which make the delivery systems of the present invention superior delivery vehicles. In the first instance, the delivery systems of this invention are substantive with skin and the mucous membrane of human beings. The term "substantive" as used throughout the specification and appended claims, indicates a cohesive interaction between the aminopolysaccharide derivative and a proteinaceous substrate. Substantivity is obtained either by having a cationic charge on the polymer which can be obtained by protonation or quaternization, or by incorporation of appropriate hydrophobic groups or combinations thereof. Thus, the delivery systems of the present invention exhibit a cohesive interaction with the proteins of the skin and mucosa of a human being.

Also, those chitosan derivatives which are cationically charged, exhibit substantive properties to keratin and other protein constituents of skin and mucosa. Thus, upon application of a cationic chitosan derivative to these tissues, the resulting film is strongly bound to the tissue, also inhibiting the loss or migration of the film and contained active(s).

The aminopolysaccharides, particularly the chitosan derivatives, are good film formers. When one of these derivatives is mixed with one or more actives and topically applied in the form of a lotion, solution, creme, ointment, spray, aerosol, powder, and the like, a polymer film readily forms which acts as a reservoir to continuously deliver the active(s) as well as protect the tissue from further injury or insult. The application of an activecontaining chitosan derivative which forms a film gives uniform distribution of the active on the tissue and prevents the migration or loss of the active from the site of application. The reservoir of active in the film helps to control the dosage at a constant level, thus controlling the rate of release. Alternatively, the active/chitosan derivative mixture may also be applied to the skin or mucosa in the form of a pre-formed film, sponge, powder or other composite as hereinafter indicated. An additional feature, is that the chitosan derivatives which are free of naturally associated proteins, heavy metals and the like, are biocompatible and non-irritating to living tissue. They also fail to elicit an inflammatory allergic, or pyrogenic response in humans after injestion or percutaneous or subcutaneous application. In addition, these chitosan derivatives form films on skin and mucosa that are imperceptible to the patient and cosmetically comfortable to wear.

The chitosan derivatives are also good humectants. It is known that moisturization of the skin and mucous membranes enhances the absorption and permeation of most pharmaceutical and therapeutic actives into those tissues. The humectant properties of these chitosan derivatives, applied to skin or mucous membranes, therefore enhance the absorption of the actives into these tissues.

As indicated above, there are two types of aminopolysaccharide derivatives which can be employed in the compositions of this invention. First are the chitosonium polymers. These chitosonium polymers are soluble in water and in mixtures of water and alcohol, and readily form humectant films, and are also substantive to skin and mucosa. These chitosonium polymers may be prepared by a number of methods including direct dissolution, spray drying, lyophilization, and the acid decrystallization process described in copending application Ser. No. 001,246, filed June 2, 1987, and its parent application of which the present application is a continuation-in-part.

However, the route of preparation of the chitosonium polymers is not critical to this invention. Examples of the chitosonium derivatives include those wherein one or more of the amino groups have been neutralized by acids, which may include: pyrrolidone carboxylic, acetic, lactic, glycolic, glyceric, mandelic, salicylic, benzoic, itaconic, malic, nicotinic, glutamic, aspartic, and the acid form of other amino acids such as N-acetyl methionine, N-acetyl tyrosine, N-acetyl glycine, N-benzoyl serine, and the like.

The second type of chitosan derivative included in this invention are covalent derivatives. These derivatives are prepared by the reaction of chitosan with one or more electrophilic reagents such as ethylene oxide, propylene oxide, glycidol, alkyl halides (from $C_1$ to $C_{24}$), glycidyl trialkylammonium salts (alkyl groups from $C_1$ to $C_{24}$), 3-chloro-2-hydroxypropyl ammonium salts, 1,3-propanesultone, haloacetates, succinic anydride, maleic anhydride, carboxylic acyl halides, the N-carboxy-alpha-amino acid anhydrides, and the like. These chitosan derivatives are readily soluble in either water, alcohol, water/alcohol mixtures, or other organic solvents such as ether, acetone, or ethyl acetate. These derivatives are good film formers, good humectants, and are substantive if cationic and/or hydrophobic groups are included in the polymer backbone.

Certain of the aminopolysaccharides which can be employed in the delivery systems of the present invention include those prepared by an acid decrystallization method as set forth in the parent applications. These aminopolysaccharides can be conveniently prepared by a method which comprises the steps of:

(a) forming a mixture of a pulverulent, partially deacetylated aminopolysaccharide and
  (1) a diluent medium in which the aminopolysaccharide is swellable but essentially insoluble; the medium comprised of:
    (i) an inert, water soluble, polar organic diluent in which the aminopolysaccharide is insoluble and the aminopolysaccharide derivative is insoluble;
    (ii) at least one organic acid which is at least partially soluble in water, is sufficiently acidic to form the ammonium salt of the aminopolysaccharide and yet not sufficiently acidic to cause hydrolysis of the aminopolysaccharide or derivative, and which is present in an amount sufficient to protonate the reactive sites of the deacetylated aminopolysaccharide;
  (2) water in an amount up to about 45 weight percent of said medium;
(b) agitating the mixture at a temperature and for a period of time to effect at least partial decrystallization; and
(c) recovering the aminopolysaccharide derivative from the mixture.

As previously indicated, a variety of derivatives of aminopolysaccharides, such as chitosan, can be prepared. These derivatives can be ionic compositions (salts) or covalent compositions.

To prepare covalent chitosan derivatives such as esters, amides and ethers, the swollen, decrystallized slurry of the chitosan salt prepared by the aforementioned method, is causticized with a stoichiometric excess of a base such as sodium hydroxide and then reacted with various electrophiles, such as ethylene oxide, glycidol, 1,2-epoxy dodecane, chloroacetic acid, succinic anhydride, and the like.

To prepare ionic derivatives in the form of salts of chitosan, the acid used in the decystallization step is chosen to provide the desired functional group and both decrystallization and derivatization, i.e. salt formation, is accomplished simultaneously. Alternatively, as indicated above, the organic acid utilized in the decrystallization step can be selected so that the chitosan is not only decrystallized but the salt is obtained containing the desired organic function present in the acid employed.

As indicated above, certain of the aminopolysaccharides are prepared by a novel, heterogeneous method for the decrystallization of aminopolysaccharides and to a variety of derivatives having properties which render them particularly attractive for use as delivery systems for pharmaceutical and therapeutic actives.

The method differs from the methods disclosed in the literature in several respects. First, the acid decrystallization process does not involve dissolving the aminopolysaccharide, such as chitosan, in an aqueous medium. Since chitosan is a very rigid molecule, only a very limited quantity can be rendered water soluble before the solution becomes too viscous to be easily handled. If the solution is further diluted to overcome the viscosity problem, the concentration of chitosan is reduced even further and hence any chemical reactions to derivatize the molecule are very inefficient and economically unattractive.

For example, in literature currently available by a company engaged in the commercial sale of chitosan in the United States, it is indicated that chitosan is soluble in solutions of most acids, particularly organic acids such as formic acid, malic, tartaric, citric, adipic, and the like. It is further indicated that in order to make a one percent solution of chitosan in water, chitosan is mixed with water and then an equal volume of an acid solution is added. For concentrated solutions of chitosan, which are indicated in the literature reference to be from about 2 to 4 percent by weight, an equal weight of acid to that of the chitosan is employed. With inorganic acids such as hydrochloric or nitric acids chitosan is soluble within the range of 0.15 to 1.1 percent acid by weight. Chitosan is not soluble in sulfuric acid and has only marginal solubility in phosphoric acid at concentrations below 0.5 percent.

Thus, prior to the invention, described in the parent applications, no method was reported in the literature whereby aminopolysaccharides could be decrystallized and derivatized in economically attractive quantities by a simple and efficient process.

A variety of acids can be used in the decrystallization process. It is, of course, necessary that the acid be at least partially soluble in water, be sufficiently acidic to form the ammonium salt of the aminopolysaccharide and yet not sufficiently acidic to cause hydrolysis of the aminopolysaccharide or derivative, and which is present in an amount sufficient to protonate the reactive sites of the deacetylated aminopolysaccharides.

Such acids can be represented by the formula:

R—(COOH)$_n$ wherein n has a value of 1 or 2 and R represents a mono- or divalent organic radical composed of carbon, hydrogen and optionally at least one of oxygen, nitrogen and sulfur. Preferred acids are the mono and dicarboxylic acids composed of carbon, hydrogen, oxygen and nitrogen, and which are at least partially water soluble, and biologically and/or pharmaceutically acceptable for use in the delivery systems of the present invention.

Accordingly, a wide variety of acids can be employed which not only affect decrystallization of chitosan, but simultaneously afford desirable derivatives as well. Illustrative acids, in addition to those previously mentioned include, among others, formic, acetic, N-acetylglycine, acetylsalicylic, fumaric, gallic, glycolic, iminodiacetic, itaconic, DL-lactic, maleic, DL-malic, methacrylic, 2-pyrrolidone-5-carboxylic, salicylic, succinamic, succinic, ascorbic, aspartic, adipic, glutamic, glutaric, malonic, nicotinic, pyruvic, sulfonyldiacetic, thiodiacetic and thioglycolic acids.

As indicated above, the medium employed in the decrystallization of the chitosan is a combination of water and an organic compound. This diluent system which is employed in the decrystallization process, is a combination of water and an organic compound. Organic compounds which are useful are those which are water soluble, in which the aminopolysaccharide is insoluble, and in which the aminopolysaccharide derivative is insoluble. Illustrative organic compound which can be employed include acetone, methanol, ethanol, n-propanol, isopropanol, tertiary butyl alcohol, acetonitrile, tetrahydrofuran, dioxane, 2-ethoxyethanol, dimethoxyethane, and the like.

The second component of the diluent medium is water and it is employed in an amount up to about 45 weight percent of the total medium, i.e., the total of the water plus the organic compound. In practice, optimum results are obtained when the diluent medium contains from about 30 to about 45 weight percent water and more preferably about 40 weight percent.

In contrast to the teachings of the prior art, this method avoids formation of a chitosan solution. By the process of the present invention the chitosan is caused to swell and accordingly viscous solutions containing only a few percent of chitosan are avoided.

The sequence of mixing the diluent medium and the deacetylated chitosan is not necessarily critical. However, it has been observed that excellent results are obtained if the diluent medium is prepared from the water and organic compound together with the acid and then the chitosan added.

As previously indicated chitosan has a very rigid structure and when it dissolves in acid solution it provides a very viscous product of low concentration of chitosan. In order for chitosan to be soluble at all, it must have a relatively large number of free primary amine groups. The chitosan employed in the present invention is deacetylated chitin and the degree of deacetylation is normally in excess of 60 percent and preferably in excess of 70 percent. The molecular weight range of the chitosan employed in the present invention can range from about 5000 to over a million and more preferably from about 10,000 to about 500,000. Particularly preferred is chitosan having a molecular weight of from about 20,000 to about 250,000.

Thus, using acids of the aforementioned formula the method can be employed in the preparation of a variety of derivatives of chitosan having utility as indicated above. For example, pyrrolidone carboxylic is an effective moisturizing agent, has a low order of irritation and accordingly is useful in delivery systems of the present invention. As indicated in the examples, such a polymer is prepared by reacting a finely ground slurry of chitosan with PCA in a polar solvent such as aqueous ethanol, or other suitable solvent that will dissolve PCA. As indicated in the parent applications, chitosonium pyrrolidone carboxylate has a large number of useful applications such as topical medical formulations. While chitosan accelerates healing the PCA is a built in humectant.

Any number of other chitosan derivatives may be made by the method of the present invention. Hence, this method for preparing chitosan salts is applicable to other organic acids that are soluble in polar organic solvents such as ethanol. For example, glycolic acid in aqueous ethanol can be reacted with chitosan to give the glycolate salt, which is also useful as a delivery system.

Moreover, the healing properties of chitin and chitosan are known. In addition to being effective fungicides, these polysaccharides are useful in accelerating the healing rate of wounds. For example, chitosonium acetate had been used as a burn covering. A solution is sprayed on the burn, forming a covering to protect the injury, while being permeable to oxygen and speeding the healing of the burn. For typical applications requiring a water-soluble form of chitosan, chitosonium acetate is employed.

When free of its naturally associated proteins, chitin is not antigenic to human tissue and may be used on, or inserted under the skin, or placed in contact with body fluids without harm. Chitin in the body is slowly attacked by lysozyme and is absorbed. In addition chitin and chitosan may be safely ingested by humans, for example, common foods such as bread, beer, wine, shrimp, crabs and mushrooms all contain some chitin.

Glycosaminoglycans (GAGS) are a class of polysaccharides that occur in the connective tissue of mammals, and include hyaluronic acid, chondroitin sulfate, and heparin. Some of these polysaccharides, hyaluronic acid in particular, have been used successfully for wound healing and tissue regeneration in both humans and laboratory animals. The exact mechanism of tissue regeneration is not known, but oligomeric metabolites of N-acetylglucosamines and glucosamine functionality present in glycosaminoglycans such as hyaluronic acid is present in chitin and chitosan, and similar wound healing and tissue regeneration properties have been reported for chitin and chitosan.

Moreover, it has been reported in the literature that growth inhibition of *Pseudomonas aeruginosa, Staphylococcus aureus,* and *Staphylococcus epidermis* on agar plates were noted with 1 % chitosan solutions in dilute acetic acid. Parallel experiments with the fungus *Candida tropicalis* and chitosan solutions also exhibited fungal growth inhibition. Similar results were reported on the fungistatic action of chitosan on plant pathogens.

In addition to the chiosonium polymers and covalent chitosan derivatives prepared as indicated above, the delivery systems of the present invention can be comprised of chitosan derivatives prepared by methods known in the literature. For example, many of the derivatives set forth in Table I of Example 6, are known compounds and can be utilized in the present invention.

Illustrative chitosan derivatives which can be prepared by the above process include, but are not limited to, chitosonium pyrrolidone carboxylate, chitosonium itaconate, chitosonium niacinate, chitosonium salicylate, chitosonium lactate, chitosonium formate, chitosonium acetate, chitosonium fumarate, chitosonium gallate, chitosonium glutamate, chitosonium maleate, chitosonium succinamate, chitosonium aspartate, chitosonium glycolate and the like.

The delivery systems of the present invention can contain a large number of pharmaceutical and therapeutic actives that can be applied topically either singularly or in combination. Examples of these actives include, but are not limited to compounds such as the following:

Anti-inflammatory analgesics such as salicylic acid, salicylate esters and salts, acetylsalicylic acid, diflunisal, acetaminophen, phenylbutazone, oxyphenbutazone, sulfinpyrazone, indomethacin, sulindac, fenoprofen, flurbiprofen, ibuprofen, ketoprofen, naproxen, mefenamic acid, floctafenine, tolmetin, zomepirac, diclofenac, piroxicam, and the like.

Local anaesthetics such as cocaine, benzocaine, tetracaine, lidocaine, bupivacaine, their hydrochloride salts, and the like.

Antibiotic agents such as penicillins, cephalosporins, vancomycin, bacitracin, cycloserine, polymyxins, colistin, nystatin, amphotericin B, mupirocim, tetracyclines, chloramphenicol, erythromycin, neomycin, streptomycin, kanamycin, gentamicin, tobramycin, amikacin, netilmicin, spectinomycin, clindamycin, rifampin, nalidixic acid, flucytosine, griseofulvin, and the like.

Sulfanilamide antibacterial agents such as sulfanilamide, sulfacetamide, sulfadiazine, sulfisoxazole, sulfamethoxazole, trimethoprim, pyrimethamine, and the like.

Antiviral agents such as vidarabine, acyclovir, ribavirin, amantadine hydrochloride, rimantadine, idoxyuridine, interferons, and the like.

Antiseptic agents such as acridine dyes, alcohols, bronopol, chlorhexidine, phenols, hexachlorophene, organic mercurials, organic peroxides, i.e., benzoyl peroxide, quaternary ammonium compounds, and the like.

Vitamin and vitamin derivatives such as Vitamin A, retinol, retinoic acid (both cis and trans), alpha-tocopherol (Vitamin E), 7-dehydrocholesterol (Vitamin D), Vitamin K, thiamine riboflavin, niacin, pyridoxine, biotin, pantothenic acid, ascorbic acid, choline, inositol, and the like.

Anti-inflammatory corticosteroids such as progesterone, hydrocortisone, prednisone, fludrocortisone, triamcinolone, dexamethasone, betamethasone, fluocinolone, and the like.

Anti-fungal agents such as miconazole, tolnaftate, naftifine hydrochloride, undecylic acid and its salts, and other heterocyclic compounds including morpholine, imidazoles and derivatives thereof.

Vasodilators such as niacin, nicotinate esters and salts, nitroglycerine, amyl nitrite, prazosin, minoxidil and diazoxide; and calcium channel blockers such as nifedipine, diltiazem, indomethacin, and the like.

Gonadal hormones such as gonadotropin-releasing hormone, human chorionic gonadotropin, gonadotropins, 17-beta-estriol, ethinyl estradiol, diethyl stibestrol, norethindrone, norethynodrel, medroxyprogesterone acetate, d-norgestrel, testosterone, fluoxymesterone, androstenedione, norethandrolone, nandrolone phenpropionate, methylandrostenediol, and the like.

Anti-histamines such as diphenhydramine, chlorpheniramine, chlorcyclizine, promethazine, cimetidine, ranitidine, and the like.

Autacoids such as prostaglandins, prostacyclin, thromboxanes, leukotrienes, angiotensins (captopril), as well as other pharmaceutically active peptides such as serotonin, endorphins, vasopressin, oxytocin, and the like.

Kerolytic agents such as benzoyl peroxide, salicylic acid, trichloroacetic acid, and piroctone, and wart treatment compounds such as salicyclic acid, trichloroacetic acid and lactic acid, singularly or in combination with anti-viral agents.

Anti-diarrhea agents such as bismuth salts (especially the subsalicylate), opium and its derivatives, diphenoxylate, difenoxin, loperamide, nufenoxole, lidamine and the like.

Anti-alopecia agents such as niacin, nicotinate esters and salts, and minoxidil.

Moisturizing agents such as lactic acid, pyrrolidone carboxylic acid, glycolic acid, water, glycerine, propylene glycol, sorbitol, other alphahydroxy carboxylic acids, and various salts of these esters and salts, and the like.

Additives for the enhanced percutaneous absorption of various pharmaceutical or therapeutic actives. Such percutaneous enhancers include propylene glycol, glycerol, urea, diethyl sebecate, sodium lauryl sulfate, sodium laureth sulfate, sorbitan ethoxylates, nicotinate esters (such as hexyl nicotinate), oleic acid, pyrrolidone carboxylate esters, (such as dodecyl pyrrolidone carboxylate), N-methyl pyrrolidone, N,N-diethyl-mtoluamide, dimethyl sulfoxide, decyl methyl sulfoxide, alkyl methyl sulfoxides, N,N-dimethyl formamide, cis-11-octadecenoic acid, 1-dodecylazacycloheptan-2-one, and 1,3-dioxacyclopentane or 1,2-dioxacyclohexane containing at least one aliphatic group of four to eighteen carbon atoms.

As indicated above, this list of pharmaceutical actives is not inclusive, but is presented merely to demonstrate the scope of the invention. A wide variety of other actives can be employed either alone or in combination.

The amount of active employed will be that amount necessary to deliver a pharmaceuticlly or therapeutically effective amount to achieve the desired result at the site of application. In practice, this will vary depending upon the particular mediciment, severity of the condition as well as other factors. In general, the concentration of the actives in the delivery systems can vary from as little as 0.0001 up to 5 percent or higher, by weight of the delivery system.

In general, the amount of chitosan derivative employed in the compositions of this invention will vary depending upon the particular pharmaceutical or therapeutic actives, the presence or absence of a diluent, the type of additives, and the like. In practice, however, it has been found that a concentration of the chitosan derivative in the composition can range from about 0.05 to about 10 weight percent, based on the total weight of the composition.

If desired, the delivery systems of this invention in addition to the chitosan derivative and active component can contain one or more pharmaceutically acceptable diluents or vehicles. In many instances the chitosan derivative itself can about 0.5 to about 30 weight percent of the system with the remainder being a diluent and optionally, other additives. Suitable diluents include among others, water, ethanol, aqueous ethanol, isopropanol, glycerine, dimethylether, carbon dioxide, butane, polyethylene glycol, ethoxylated or propoxylated glucose, sorbitol derivatives, and the like.

Although the inclusion of the chitosan derivatives in the delivery systems of this invention usually avoids the necessity for using ointments, oils and other esthetically undesirable carriers, in some instances it may be helpful to include such compounds.

In practice, the delivery systems of the invention are readily formulated by blending a solution or suspension of one or more of the active components with a solution or suspension of the chitosan derivative.

In the present invention the active or actives are dissolved or suspended in an appropriate solvent or diluent such as water, ethyl alcohol, isopropyl alcohol, diethylether, dimethylether, acetone, ethyl acetate, or mixtures thereof, and mixed with a solution or suspension of the desired chitosan derivative also in an appropriate solvent or diluent. Other adjuvant ingredients such as glycerine, propylene glycol, sorbitol, preservatives, stearic acid, cetyl alcohol, other high molecular weight alcohols, surfactants, menthol, eucalyptus oil, other essential oils, fragrances, penetration enhancers, and the like to give stable cremes, ointments, lotions, aerosols, solutions, may also be included.

Alternatively, solutions or mixtures of the actives with the chitosan derivatives may be prepared with or without some of the adjuvant ingredients, and these solutions or mixtures may be fabricated into films, rods, sheets, sponges or fibers for use as suppositories, medicated sutures, medicated sheets, medicated bandages, patches, and the like.

Examples 1 to 6 which follow are directed to the preparation of various chitosan derivatives using the acid decrystallization process. Examples 7 to 35 are directed to the preparation of delivery systems of the present invention using derivatives prepared by the acid decrystallization method as well as known derivatives prepared by methods disclosed in the literature.

In the following examples, distilled water and absolute ethanol were used as indicated. The active is dissolved in alcohol or alcohol/water, and mixed with an aqueous solution of the specified chitosan derivative. The chitosonium polymers were prepared by the acid decrystallization technique described in copending patent application Ser. No. 001,246, filed June 2, 1987. Unless otherwise indicated the solution viscosity of the chitosan polymers is between about 5 and 5000 cP at 1% and 20° C., as measured using a Brookfield viscometer model LVT, spindle #2.

The following examples are illustrative:

EXAMPLE 1

Preparation of Carboxymethylchitosan by the acid Decrystallization Procedure

A 500 ml, four-necked round bottom flask was fitted with a stirring rod and paddle, a serum cap, a subsurface nitrogen feed, and a Claisen head fitted with a pressure-equalizing addition funnel and an Allihn condenser with a mineral oil bubbler. The flask was charged with 10 g of chitosan (ground to pass a 0.5 mm screen), 46 ml of isopropanol, and 24 ml of water. While stirring the slurry, it was purged with nitrogen for 40 minutes to remove entrained oxygen.

A solution of 6.0 g of glacial acetic acid in 25 ml of isopropanol was added dropwise to the slurry over a 5 minute period, followed by 15 ml of water. The swollen chitosan slurry was then stirred under nitrogen for 30 minutes. Thereafter 26.82 g of 50% aqueous sodium hydroxide was added by syringe dropwise to the slurry under nitrogen, and the causticized slurry was stirred for 90 minutes.

A solution of 11.2 g of monochloroacetic acid in 25 ml of isopropanol was added to the slurry, and the mixture was refluxed for four hours under nitrogen. The slurry was then cooled to room temperature and neutralized with a solution of 1.5 g of glacial acetic acid in 25 ml of isopropanol. The polymer was collected by vacuum filtration, and washed in a Waring blender, four times with pure acetone. The polymer was dried in vacuo at 50° C. to give a granular olive-grey solid, 19.62 g, which was readily soluble in water to give a solution free of insolubles. The polymer was also soluble in dilute aqueous sodium hydroxide and aqueous acetic acid.

As a control experiment, the above procedure was repeated exactly, except that the 6.0 g of glacial acetic acid used in the acid decrystallation step was omitted, and the caustic charge was correspondingly reduced from 25.82 g to 18.82 g of 50% aqueous sodium hydroxide. The resulting olive-grey solid, (18.82 g) was found to be swollen but not soluble in water, dilute aqueous sodium hydroxide, or dilute aqueous acetic acid. These experiments demonstrate the use of acid decrystallization in preparing completely water-soluble covalent derivatives of chitosan by a heterogeneous process.

EXAMPLE 2

Preparation of 2-pyrrolidone-5-carboxylate derivative

In this example, 2-pyrrolidone-5-carboxylic acid, hereinafter referred to as PCA, was prepared and mixed with chitosan in varying ratios. 3.36 g of PCA was dissolved in 75 ml of absolute ethanol. Three 125-ml Erlenmeyer flasks were charged with 2.5 g of 0.5 mm mesh chitosan having a degree of deacetylation of about 80%, and 37.5 ml, 25 ml, and 12.5 ml of the alcoholic PCA solution were added to each, respectively, and the slurry diluted to 50 ml with absolute ethanol. Each slurry was stirred for 2 hours. The molar ratios of the three solutions were respectively 1:1, 0.67:1, and 0.33:1 of PCA to chitosan.

Each slurry was vacuum-filtered and the residue was washed with pure acetone. The mass of each batch of product was 2.5 g, and the product was completely water insoluble. The product had the characteristics and behaviour of native, unreacted chitosan.

The three 2.5 g recovered chitosan samples were combined and placed in a 250-ml beaker with 100 ml of 95% ethanol (7.5 g in 100 ml).

3.5 g of PCA were dissolved in 16 ml of water, and the acid solution was added to the ethanol slurry of chitosan (7.5 g). The chitosan became swollen and curdlike. The slurry was stirred for a few minutes, and 80 ml of 95% ethanol were added. The curd-like polymer precipitated, and the slurry was vacuum-filtered. By the consistency of the polymer, recovery could be made by either decantation or centrifugation. The polymer was then washed three times with pure acetone to desiccate it. The polymer was placed in a tared crystallizing dish and dried in vacuo overnight at 50° C. A small portion of polymer was checked for water-solubility before vacuum drying and found to be soluble. A small amount of insoluble material remained suspended in solution. The pH of the solution was 6.0.

EXAMPLE 3

Preparation of chitosonium pyrrolidone carboxylate

A 500 ml flask was fitted with a stirring paddle and motor, and charged with 10.0 g of chitosan (degree of deacetylation about 80%, ground to 0.5 mesh) and 100 ml of acetone. A slurry of 8.0 g of DL-2-pyrrolidine-5-carboxylic acid in 33 ml of water was added, followed by 43 ml of acetone and 35 ml of water. The slurry was stirred for one hour.

The slurry was vacuum-filtered, and the polymer was washed in a Waring blender once with 300 ml of 4:1 (by volume) acetone/water, and twice with pure acetone. The polymer was a granular greenish-grey solid, which was dried in vacuo at 50° C. to yield 16.5 g of product. Correcting for volatiles in the starting material and product, the mass gain MS of chitosonium pyrrolidone carboxylate was found to be 0.82. The polymer was readily soluble in water to give a clear, amber solution with no insolubles. Brookfield viscosity (1% solution)=660 cP (30 rpm, Spindle#2).

EXAMPLE 4

Preparation of chitosonium itaconate

A 600 ml beaker was fitted with a stirring paddle and motor, and charged with 15.0 g of chitosan (degree of deacetylation about 80%, ground to 0.5 mm mesh), 180 ml of water, and 120 ml of acetone. While stirring the slurry, 12.1 g of itaconic acid (Aldrich) was added as a powder over a few minutes. The slurry was then stirred for three hours.

The slurry was allowed to settle, and 300 ml of supernatant was decanted. Fresh acetone (225 ml) was added, the slurry was stirred for 15 minutes. The polymer was collected by vacuum filtration, and dried in vacuo at 50° C. to yield 19.0 g of product. Correcting for volatiles in the starting material and product, the mass gain MS of chitosonium itaconate was found to be 0.30. Chitosonium itaconate is insoluble in water at room temperature, but dissolves at elevated temperature (about 75° C.), and remains dissolved after cooling.

EXAMPLE 5

Preparation of chitosonium salicylate

A 250 ml beaker was fitted with a stirring paddle and motor, and charged with 3.0 g of chitosan (degree of deactylation about 0.80, ground to 0.5 mm) and 25 ml of isopropanol. A solution of 2.45 g of salicylic acid and 24 ml of isopropanol was added to the slurry, followed by 15 ml of water. The slurry began to thicken and swell. After stirring for several minutes, the thick, sticky slurry was placed in a Waring blender and desiccated with acetone (2×250 ml). The polymer was collected by vacuum-filtration and dried in vacuo at 50° C., yield 4.23 g of product. The polymer was partly soluble in water at room temperature, but dissolves at elevated temperatures (about 75° C.), and thereafter remains completely soluble after cooling to room temperature.

EXAMPLE 6

Preparation of other chitosonium derivatives

In a manner similar to that employed in the above examples, and using the basic procedure described for chitosonium pyrrolidone carboxylate, other chitosonium salts were prepared. These salts were readily soluble in water at room temperature, except for the malate, maleate, itaconate, salicylate, fumarate, and succinate salts which required heating at about 75° C. to effect dissolution. The product from the reaction of glyoxylic acid is insoluble in water, presumably because of Schiff base formation as described by R.A.A. Muzzarelli and F. Taufani (Pure & Appl. Chem., 54 (11), 2141 (1982). The products from the reaction of acrylic, citric, gallic, 4-hydroxybenzoic, methacrylic, and vanillic acids are only slightly soluble in water, because of limited reaction efficiencies, as indicated in the low mass gain DS values or these products.

The acids which were used in the preparation of the chitosonium derivatives are set forth below in Table I:

TABLE I

Organic acids

Acetic
N-Acetyl-L-cysteine
N-Acetyl glycine
Acetylsalicylic,
Acrylamido-2-methane sulfonic
Acrylic
Adipic
L-Aspartic
Citric
Fumaric
2-Furoic
Gallic
L-Glutamic
Glutaric,
Glycolic
Glyoxylic
Hydrochloric
4-Hydroxybenzoic
Iminoacetic
Itaconic,
3-Ketoglutaric
DL-Lactic,
Maleic,
Malonic
Methacrylic
Methanesulfonic
Nicotinic
Oxiniacic
Picolinic
2,3-Pyridinedicarboxylic
2-Pyrrolidone-5-carboxylic
Pyruvic
Saccharin,
Salicyclic,
Succinamic,
succinic
Sulfamic
Sulfanilic
Sulfonyldiacetic
L-Tartaric
Thioacetic
Thiolactic
Vanillic Examples 7-35 which follow, illustrative delivery systems of the present invention.

EXAMPLE 7

Preparation of a chitosan-based anti-alopecia lotion 0.20 g of minoxidil and 0.12 g of nicotinic acid are dissolved in a solution of 3.0 g of ethanol and 1.7 g of water. 5.0 g of 2.0% chitosonium niacinate in 90:10 water/ethanol are added, and after vigorous mixing, a clear colorless solution was obtained which is useful as a scalp/hair lotion to prevent or treat alopecia by vasodilation of capillaries in the hair follicles. Both minoxidil (2.0%) and nicotinic acid (niacin) are known to be vasodilators and may well act synergistically.

EXAMPLE 8

Preparation of a chitosan-based burn treatment lotion 0.15 g of ethyl 4-aminobenzoate (benzocaine) are dissolved in 3.85 g of ethyl alcohol and 1.0g of water. 5.0 g of 2.0% aqueous chitosonium pyrrolidone carboxylate are added, and after vigorous mixing, a clear, colorless solution was obtained. This lotion is useful in the treatment of sunburns and other minor burns. The benzocaine (1.5%) is a local anesthetic which would alleviate pain and discomfort, and chitosonium pyrrolidone carboxylate is an excellent humectant which moisturizes the skin.

EXAMPLE 9

Preparation of a chitosan-based antibiotic lotion 0.055 g of chloamphenicol are dissolved in 2.0 g of ethyl alcohol and 2.95 g of water. 5.0 g of 2.0% aqueous chitosonium pyrrolidone carboxylate are added, and after vigorous mixing, a clear, colorless solution is obtained, useful in the antibiotic treatment of a variety of topical bacterial, chlamydial, and rickettsial infections (0.55% chloramphenicol).

EXAMPLE 10

Preparation of chitosan-based antibacterial sulfa lotion 0.027 g of sulfadiazine are dissolved in 4.73 g of ethyl alcohol, and mixed with 5.0 g of 2% aqueous chitosonium pyrrolidone carboxylate, giving a clear colorless solution (0.27% sulfadiazine). Sulfadiazine is used topically in burn treatment to control *Pseudomonas aeruginosa* infections.

EXAMPLE 11

Preparation of chitosan-based anti-fungal lotion 0.06 g of miconazole nitrate are dissolved in 4.5 g of ethyl alcohol and 0.44 g of water, and mixed with 5.0 g of 2% chitosonium pyrrolidone carboxylate in 90:10 water/alcohol, giving a clear, colorless solution (0.6% miconazole). This lotion is useful in the treatment of a variety of topical fungal infections, including Athlete's foot.

EXAMPLE 12

Preparation of chitosan-based corticosteroid lotion 0.013 g of hydrocortisone are dissolved in 4.99 g of ethyl alcohol, and mixed with 5.0 g of 2% aqueous chitosonium pyrrolidone carboxylate, giving a clear, colorless solution. This solution (0.13% hydrocortisone) is useful in the topical treatment of a variety of local inflammatory diseases and pruritis. Substituting 0.015 g of dexamethasone for 0.013 g of hydrocortisone in this formulation yields a clear, colorless solution of 0.15% dexamethasone, a fluorinated steroid, also used in the treatment of topical inflammatory diseases and general inflammation.

EXAMPLE 13

Preparation of a chitosan-based non-steroid anti-inflammatory lotion 0.50 g of ibuprofen are dissolved in 4.5 g of ethyl alcohol, and mixed with 5.0 g of 2% chitosonium niacinate in 90:10 water/alcohol, giving a clear, colorless solution (5.0% ibuprofen). This solution is useful for a variety of localized inflammations, including topical treatment of muscle pain, as well as tendon, ligament, and muscle sprains.

EXAMPLE 14

Preparation of chitosan-based antihistamine lotion 0.025 g of chlorpheniramine maleate are dissolved in 0.05 g of glycerine and 9.925 g of 1.5% aqueous chitosonium pyrrolidone carboxylate, giving a clear, colorless solution (0.25% chlorpheniramine maleate). This lotion is useful in the treatment of rashes and inflammation due to allergic reactions.

EXAMPLE 15

Preparation of a chitosan-based anti-acne lotion 0.01 g of retinoic acid are dissolved in 4.99 g of ethyl alcohol, and mixed with 5.0 g of 2% aqueous chitosonium pyrrolidone carboxylate, and vigorously shaken. With trans-retinoic acid (0.1% retinoic acid) an opaque, opalescent, homogeneous yellow solution is obtained. With cis-retinoic acid, a clear, homogeneous yellow fluid is obtained. Both isomers of retinoic acid are useful in the topical treatment of acne. Both isomers of retinoic acid are compatible with the chitosan derivatives of the present invention.

EXAMPLE 16

Preparation of chitosan-based topical antioxidant 0.02 g of alpha-tocopherol are dissolved in 6.0 g of ethyl alcohol, and mixed with 4.0 g of 2% aqueous chitosonium salicylate to give a translucent, opalescent, homogeneous white fluid. This lotion (0.2% alpha-tocopherol) is used as a topical antioxidant for skin, to retard and inhibit the deleterious effects of sunlight and oxygen on skin.

EXAMPLE 17

Preparation of a chitosan-based kerolytic lotion 2.0 g of salicylic acid are dissolved in 5.0 g of ethyl alcohol and mixed with 3.0 g of 10% aqueous chitosonium salicylate (very low molecular weight, 1% solution=5cP at 20° C.) to give a clear, colorless solution of 20% salicylic acid. This solution is useful as a kerolytic lotion for the treatment of acne, psoriasis, and similar skin diseases.

EXAMPLE 18

Preparation of chitosan-based benzoyl peroxide lotion 0.11 g of benzoyl peroxide are dissolved in 4.89 g of propylene glycol (or 4.89 g of GLUCAN E-20), and mixed with 5.0 g of 2% aqueous chitosonium salicylate to give an opaque, homogeneous white creme. This creme is useful as a kerolytic agent, topical antibacterial and disinfectant for the treatment of acne.

EXAMPLE 19

Preparation of a chitosan-based antibiotic lotion with erthromycin o.05 g of erthromycin and 0.009 g of 2-pyrrolidone-5-carboxylic acid are dissolved in 5.00 g of absolute ethanol. 5.00 g of 2.0% aqueous chtiosonium pyrrolidone carboxylate are added, and after vigorous mixing, a clear, colorless solution is obtained, useful in a variety of topical bacterial infections (0.5% erythromycin).

EXAMPLE 20

Preparation of chitosan-based topical lotion with neomycin B 0.05 g of neomycin B are dissolved in 5.00 g of water and mixed with 5.00 g of 2% aqueous chitosonium pyrrolidone carboxylate, giving a clear, colorless solution. This solution (0.5% neomycin B) is useful in the treatment of topical infections.

EXAMPLE 21

Preparation of a chitosan-based corticosteroid lotion 0.0225 g of triamcinolone acetonide are dissolved in 4.99 g of ethyl alcohol and mixed with 5.09 g of 2% aqueous chitosonium lactate, giving a clear, colorless solution. This solution (0.225% triamcinolone acetonide) is useful in the topical treatment of a variety of local inflammatory diseases.

EXAMPLE 22-35

Preparation of topical formulations using covalent chitosan derivatives

Each of the above formulations was repeated, except that 2% aqueous glycidyl trimethylammonium chloride/glycidol modified chitosan as described in European Patent No. 0 115 574 was substituted for the 2% aqueous chitosonium pyrrolidone carboxylate. In each case, the mixture was clear, compatible, and homogeneous.

Although the invention has been illustrated by the preceding examples, it is not to be construed as being limited to the materials employed therein, but rather, the invention relates to the generic area as herein before disclosed. Various modifications and embodiments thereof can be made without departing from the spirit or scope thereof.

What is claimed is:

1. A biocompatible, substantive, film-forming delivery system for the delivery of pharmaceutical or therapeutic actives to a desired topical site of a subject, said system being comprised of pharmaceutical of therapeutic actives and from about 0.1 to about 99.99 weight percent of the system of at least one aminopolysaccharide selected from the group consisting of:
   (1) chitosonium polymers, and
   (2) covalent chitosan derivatives, and wherein said system after delivery to said site, provides a non-irritating, substantive, gas permeable, film from which the actives are available for treatment of said subject at said site.

2. The delivery system of claim 1 wherein said aminopolysaccharide is a chitosonium polymer.

3. The delivery system of claim 1 wherein said aminopolysaccharide is a covalent chitosan derivative.

4. The delivery system of claim 1 wherein said aminopolysaccharide is chitosonium pyrrolidone carboxylate; chitosonium niacinate, chitosonium itaconate, chitosonium salicylate, chitosonium lactate or chitosonium glycolate.

5. The delivery system of claim 1 wherein said aminopolysaccharide is blended with hyaluronic acid.

6. The delivery system of claim 1 which contains a pharmaceutically acceptable diluent.

7. The delivery system of claim 1 which is in the form of a film.

8. The delivery system of claim 1 which is in the form of a gel.

9. The delivery system of claim 1 which is in the form of a patch.

10. The delivery system of claim 1 which is in the form of an aerosol.

11. The delivery system of claim 1 which is in the form of a suppository.

12. The delivery system of claim 1 which is in the form of a fibre.

13. The delivery system of claim 1 which is in the form of a rod.

14. The delivery system of claim 1 which is in the form of microspheres.

15. The delivery system of claim 1 which is in the form of a hemostatic device or solution.

16. The delivery system of claim 1 which is a device selected from the group consisting of a pad, sponge and suture.

17. The delivery system of claim 16 which is in the form of a suture.

* * * * *